United States Patent [19]

Flick

[11] Patent Number: 5,579,539
[45] Date of Patent: Dec. 3, 1996

[54] DISPOSABLE, ELASTOMERIC GLOVE

[76] Inventor: Conrad Flick, 3715 1/2 State St., Bettendorf, Iowa 52722

[21] Appl. No.: 347,191

[22] Filed: Nov. 21, 1994

Related U.S. Application Data

[63] Continuation-in-part of Ser. No. 916,437, Jul. 21, 1992, Pat. No. 5,365,608.

[51] Int. Cl.$^6$ .................................................. A41D 19/00
[52] U.S. Cl. ............................ 2/168; 2/161.7; 2/162
[58] Field of Search .......................... 2/161.6, 161.7, 2/168, 158, 159, 160, 168, 169, 167, 162, 161.8, 901

[56] References Cited

U.S. PATENT DOCUMENTS

| | | | |
|---|---|---|---|
| 1,878,127 | 3/1926 | Hynes | 2/158 |
| 2,325,482 | 7/1943 | Curran | 2/159 |
| 2,821,718 | 2/1958 | Hall et al. | 2/162 |
| 4,099,270 | 7/1978 | Jabour | 2/168 |
| 4,218,778 | 8/1980 | Stansbury | 2/168 |
| 4,399,567 | 8/1983 | Weon Joong | 2/161.6 |
| 4,441,213 | 4/1984 | Trumble et al. | 2/168 |
| 4,464,796 | 8/1984 | Hassenberger et al. | 2/162 |
| 4,718,125 | 1/1988 | Derda et al. | 2/158 |
| 4,845,780 | 7/1989 | Reimers et al. | 2/161.7 |
| 4,876,747 | 10/1989 | Coffey et al. | 2/161.7 |
| 5,020,160 | 6/1991 | Cano | 2/159 |

*Primary Examiner*—Amy B. Vanatta
*Attorney, Agent, or Firm*—Bradford E. Kile

[57] ABSTRACT

A disposable elastomeric glove having a distinct protuberance in proximal position with respect to an abductor pollicis longus muscle of a wearer and between a proximal edge of a cuff and a wrist region of the glove. The protuberance is grasped to safely remove the glove from the hand.

7 Claims, 4 Drawing Sheets

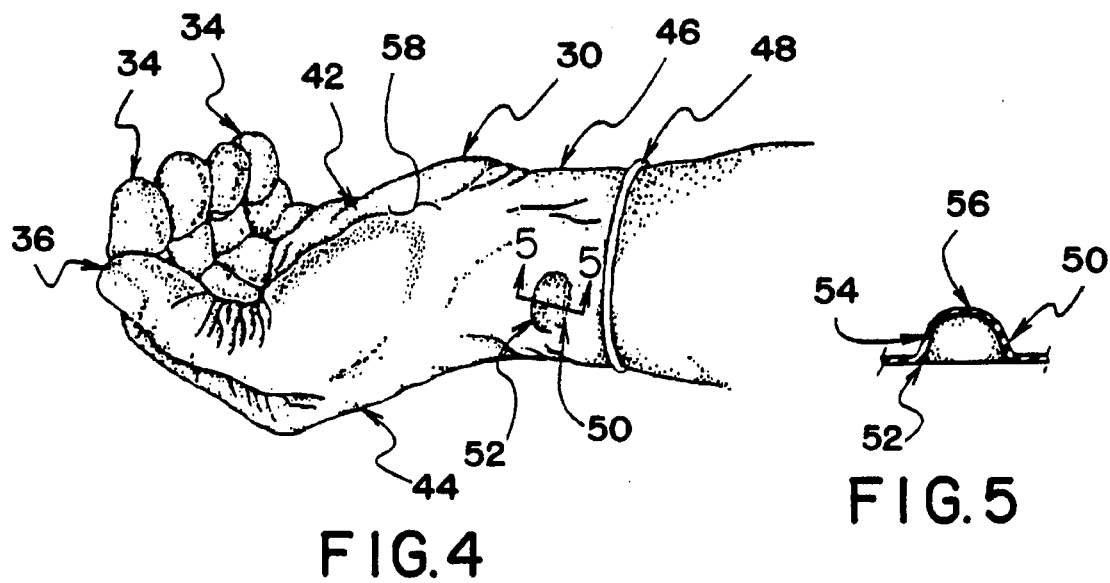
FIG.4
FIG.5
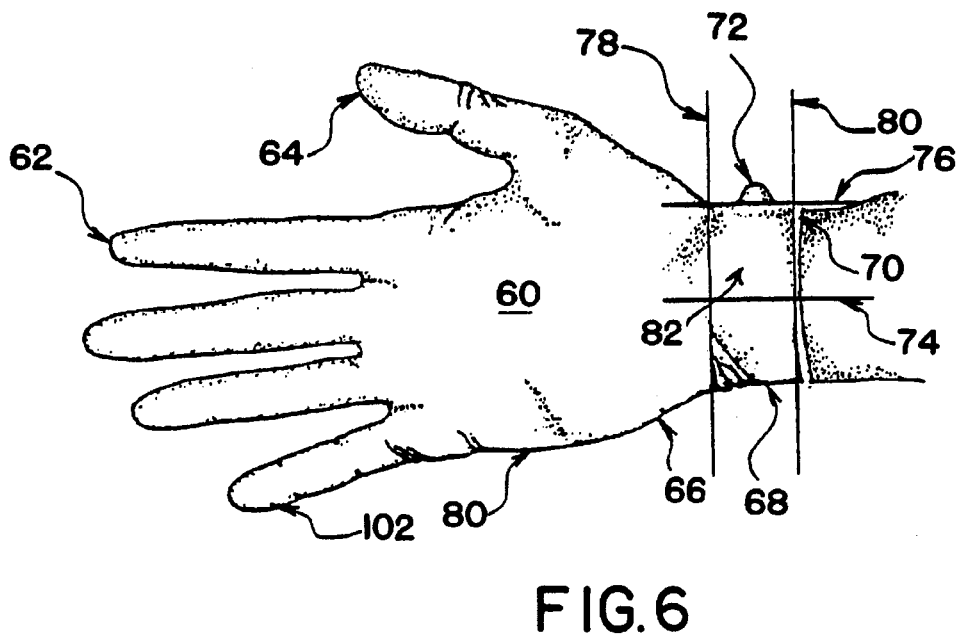
FIG.6

DISPOSABLE, ELASTOMERIC GLOVE

This is a continuation-in-part of application Ser. No. 07/916,437, filed Jul. 21, 1992; now U.S. Pat. No. 5,365,608.

BACKGROUND OF THE INVENTION

This invention relates to a novel, disposable, elastomeric glove. More specifically, this invention relates to a disposable elastomeric glove which may be facilely removed by a wearer while hygienically maintaining isolation integrity of the wearer's hands from any contaminant on the exterior surface of the glove.

The use of an elastomeric glove by medical and laboratory professionals to prevent the tactile transfer of foreign materials during various procedures has been known for years. Originally a predominant interest of health care professionals was to maintain a sterile interface to isolate a patient from contamination by the health care provider. More recently, with the explosion of body fluid transmitted diseases, such as acquired immune deficiency syndrome (AIDS), etc., health care professionals are equally concerned about maintaining uncompromising isolation integrity with respect to the body fluid of a patient. This has dramatically increased the need for and use of disposable, elastic gloves not only by traditional health care providers such as operating theater personnel but also in dental offices, external medicine, etc. Moreover, in ever expanding arenas of human contact such as sports trainers, law enforcement, beauticians, etc., wearing disposable rubber gloves is becoming a precaution of preference.

Protective gloves are typically formed of a thin gauge elastomeric material, such as latex or natural rubber, so as not to impair a wearer's tactile sense. The elastomeric material is designed to stretch around and intimately conform to the hand of a wearer and thus not interfere with the performance of a delicate procedure by bunching of excess material. This close conforming fit by a relatively thin gauge elastomeric material makes removal of the gloves somewhat difficult.

The foregoing advantages attendant the fabrication of elastomeric gloves composed of a thin film with an intimate fit are highly desirable in terms of glove utility but present significant complications when it is desirable to quickly remove and/or replace a glove. In this, a snug fitting glove is not easily removed and is subject to stretch and binding at various locations of a wearer's hand. This complication is exacerbated when it is realized that there may be fluid on the exterior surface of the glove and it is essential not to allow any contaminant to contact a wearer's skin.

In the past, there have been various methods for removing elastomeric gloves. One common technique is to insert a thumb or finger of an opposite hand under a beaded edge of a cuff of the glove in a central location on the palm side of the glove and peel the glove from the hand. This method favorably inverts the glove during the removal process to essentially contain most of the contamination fluid within the inverted glove. One disadvantage occasioned with this method arises with the insertion of the opposing, gloved finger within the cuff opening. During most procedures involving elastomeric gloves, the exterior surface of the glove is exposed to biological or chemical contaminants or the like. When utilizing the foregoing technique of digital glove removal it becomes virtually impossible to be certain that physical contact will not occur with the wrist or arm by the contaminated, gloved finger due to the tight fitting cuff about the wrist. Moreover, a nail of an inserting thumb or finger may accidentally scrape exposed wrist skin through the glove material. With a growing concern about AIDS, contacting any tissue surface of a health care provider with contaminated, gloved surfaces is highly undesirable.

Another method of doffing a rubber glove is to grasp cuff material with one's fingertips and distally pull the glove. A disadvantage of this technique is that if the glove material is taught, it is difficult to grasp and, once grasped, tends to bind at the base of the palm. Removal from this point is difficult as the muscles of the thenar eminence restrict movement and impair reverse rolling of the glove. Moreover, the material is thin and susceptible to tearing if undue force is applied. Moreover, a fingernail of the wearer may puncture the glove.

Several designs have previously been known which implement a tab component as a means of securement and removal. In one such embodiment, a cusp shaped tab element is integrally formed with the front and back panels of a glove at the proximal cuff end to facilitate removal. In still another embodiment, a tab is formed by a small flat extension of the elastomeric glove material at the proximal edge of the glove opening. This flap lies abutting the wrist in most instances. A problem common to previously known tab designs arises in the removal by attempting to grasp the tab in the wrist abutting position without contacting unprotected skin by the opposing gloved hand.

In another embodiment, the tab lies in a similar placement and is used to secure the free end of a cuff portion for tightening the cuff when the glove is on the wearer's hand. If the tab is in contact with the glove surface, grasping the tab edge may be difficult with the other gloved hand. In addition the manufacture involves attachment of a second element; the actual tab and/or the removable adhesive shield.

Another embodiment actually establishes a predetermined tear line with an adjacent gripping area, such as a textured area, tab, hole, or the like. A similar problem of contacting unprotected skin by the opposing, gloved hand when attempting to remove the glove exists. Once the glove is removed, the glove has no structured shape and the outer contaminated surfaces are exposed.

In yet another embodiment, a raised loop is attached to the back portion of the wrist to facilitate removal by pulling distally with opposing hand or with a separate hook device to avoid exposed skin contact. This design however, does not avoid binding at the wrist in the region of the thenar eminence.

Although previously known elastomeric gloves have received considerable use, it would be highly desirable to provide a glove which would be safe in use, easy to remove, inexpensive to manufacture, and adapts to various hands. The foregoing should be advantageously achieved with a unit which is efficient in design and possesses a high degree of isolation integrity from patient fluids. Still further, it would be desirable to provide an elastomeric glove with the foregoing characteristics and in addition can be worn on either hand and is inside-out reversible.

The difficulties and limitations suggested in the preceding and desired features are not intended to be exhaustive but rather are among many which may tend to reduce the effectiveness and user satisfaction with prior disposable, elastomeric gloves. Other noteworthy problems and limitations may also exist; however, those presented above should be sufficient to demonstrate that disposable, elastomeric gloves appearing in the past will admit to worthwhile improvement.

OBJECTS AND BRIEF SUMMARY OF THE INVENTION

It is therefore a general object of the invention to provide a novel disposable, elastomeric glove which will obviate or minimize problems of the type previously described. It is a specific object of the invention to provide a disposable, elastomeric glove having an integral provision which facilitates safe, selective removal.

It is another object of the invention to provide a disposable, elastomeric glove which may be facilely removed in a manner which utilizes glove inversion to isolate contaminated fluid from a user and those around the user.

It is still another object of the invention to provide a novel, elastomeric glove having a facile removal capability which does not interfere nor distract from performing conventional health care procedures.

It is a related object of the invention to provide a disposable, elastomeric glove having a doffing means operable for insuring the safe removal of the glove.

It is still another object of the invention to provide a novel, disposable, glove which will be operable to be safely and rapidly doffed without catching and stretching over the abductor pollicis longus muscle.

It is yet another object of the invention to provide a disposable, elastomeric glove which requires no external devices or persons to assist in removal.

It is still another object of the invention to provide a disposable, elastomeric glove which permits the safe donning and doffing of the glove while being suitable for manufacture by previously known dipping techniques.

It is yet still another object of the invention to provide a disposable, elastomeric glove which may be ambidextrous and/or inside-out reversible.

It is a further object of the invention to provide a disposable, elastomeric glove which may be facile adjusted during use without contaminating a wearer.

It is yet a further object of the invention to provide a pair of disposable, elastomeric gloves which are operable to be simultaneously removed as a pair.

BRIEF SUMMARY OF A PREFERRED EMBODIMENT OF THE INVENTION

A preferred embodiment of the invention which is intended to accomplish at least some of the foregoing objects entails a disposable elastomeric glove having a distinct protuberance in proximal position with respect to the abductor pollicis longus muscle and between a proximal edge of a cuff and a wrist region of the glove.

THE DRAWINGS

Other objects and advantages of the present invention will become apparent from the following detailed description of preferred embodiments thereof taken in conjunction with the accompanying drawings wherein:

FIG. 4 is an axonometric view of one first embodiment of the subject disposable, elastomeric glove invention wherein a protrusion is positioned between the cuff and abductor pollicis longus muscle to facilitate removal of the glove from a wearer's hand;

FIG. 5 is an enlarged partial cross-sectional view taken along section line 5—5 in FIG. 4 and discloses one embodiment of the protrusion configuration as comprising a generally hollow, conical segment having an elongate or elliptical base;

FIG. 6 is a plan view of a disposable, elastomeric glove in accordance with the subject invention wherein the protrusion is located at an edge of a zone of optimum placement and thus the glove may be used with equal facility upon a wearer's right hand or left hand;

Figure 11:
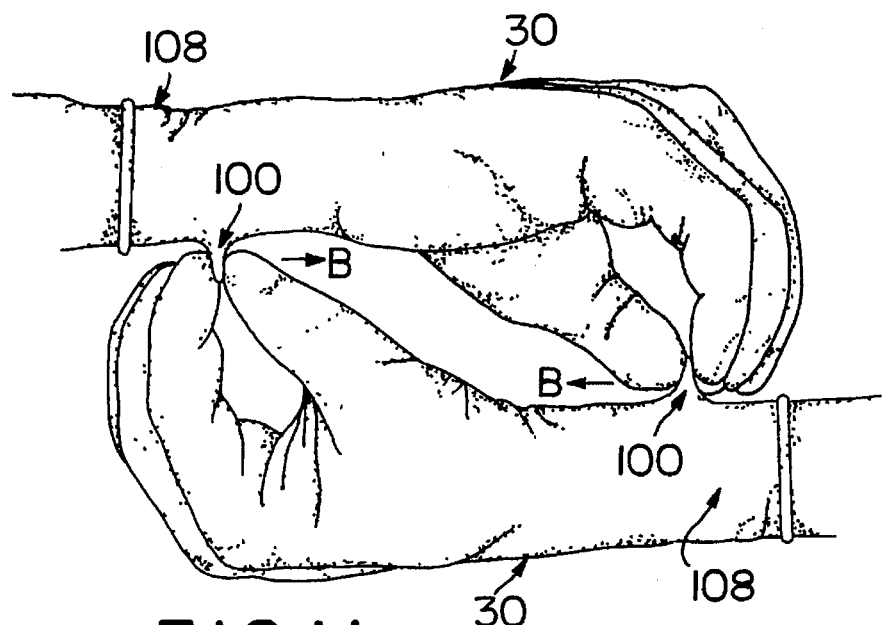
Figure 12:
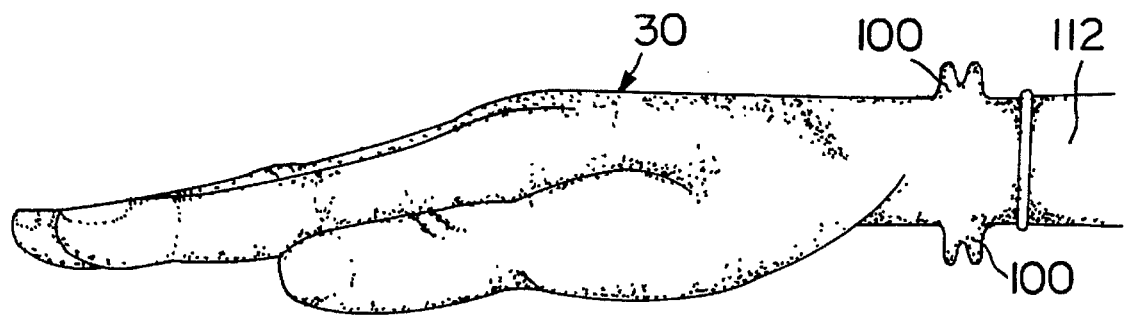

FIG. 11 is side view of a disposable, elastomeric glove in accordance with an alternative embodiment of the subject invention wherein a wearer is beginning the simultaneous removal process by grasping a protrusion or tab of both gloves with a thumb and index finger of an opposing gloved hand; and FIG. 12 is a side view of an ambidextrous disposable, elastomeric glove in accordance with the alternative embodiment showing two protrusions located on opposing cuff portions of the glove.

DETAILED DESCRIPTION

Context of the Invention

Figure 1:
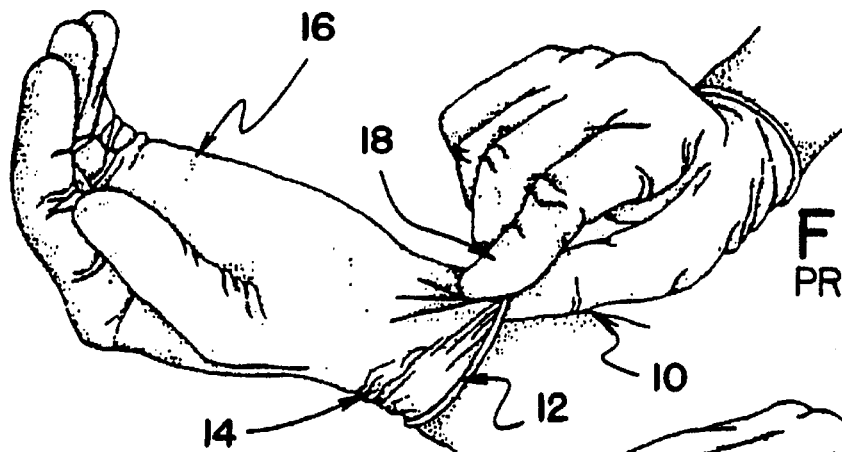
FIG. 1 is an axonometric view of a prior art glove and one technique of removal wherein a rolled cuff of the disposable, elastomeric glove is grasped between a thumb and forefinger of an opposing hand in approximately a center wrist portion of the glove.
Figure 2:
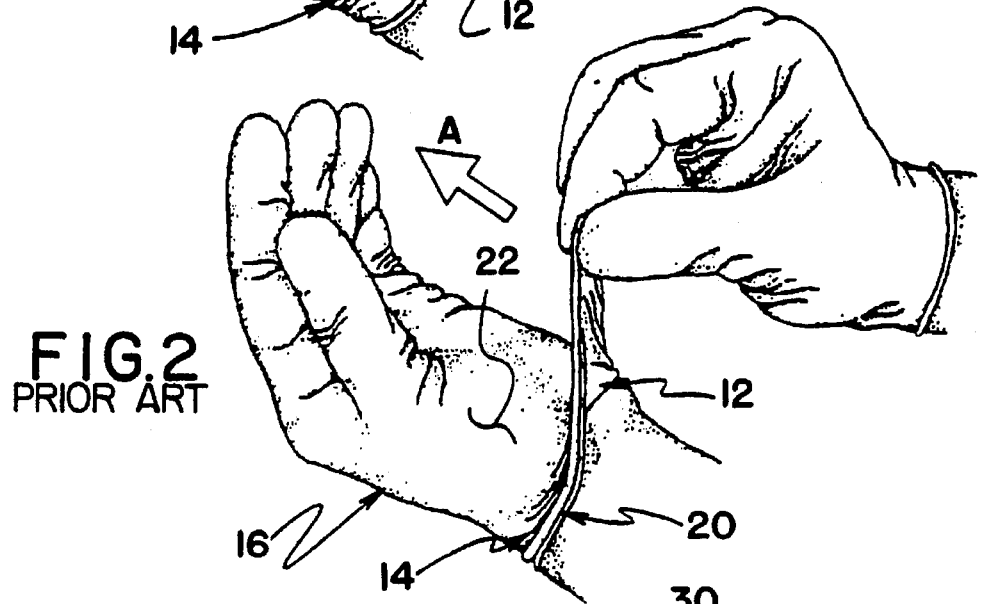
FIG. 2 is another prior art view in sequence with respect to FIG. 1, and discloses a wearer attempting to remove the disposable, elastomeric glove by pulling upwardly and distally on the cuff; however, it will be noted that an edge or lip adjacent the abductor pollicis longus muscle becomes bound and restricts easy removal of the glove.

Referring now particularly to the drawings, wherein like reference characters refer to like parts and particularly to FIGS. 1 and 2, axonometric views will be seen of a general operative environment of the subject invention. In this regard, conventional disposable, elastomeric gloves are shown worn upon the hands of a health care provider, sports trainer, policemen, etc. Following an operative or an examination procedure, or during such procedures, a health care or other professional provider may decide to remove the disposable gloves. In this event, a conventional technique has been to insert a wearer's thumb 10 beneath a lip 12 of a cuff portion 14 of the elastomeric glove 16. The cuff 12 is then grasped between the thumb 10 and forefinger 18 of the wearer's free hand, and as depicted in FIG. 2, an edge of the cuff is lifted and pulled distally in the general direction of arrow A.

In certain instances, the thin elastomeric glove 16 tends to stretch during the removal operation and the ribbed edge 12 of the cuff 14 tends to bind at the wrist region 20 of a wearer. In this connection, the abductor pollicis longus muscle 22 of a wearer's hand tends to form a crease at its base with respect to a wearer's wrist. This crease tends to exacerbate binding of the lip 12 of the cuff 14 and prevent the glove from being easily removed. In this respect, as resistance is offered, a user typically applies more force in the general direction of arrow A and often the elastomeric glove tends to stretch and create more resisting force until the force of removal exceeds that of the binding action. In certain instances, the glove may unexpectedly release and flip off in an erratic fashion spraying contaminants into the ambient environment.

Disposable Elastomeric Glove

Figure 3:
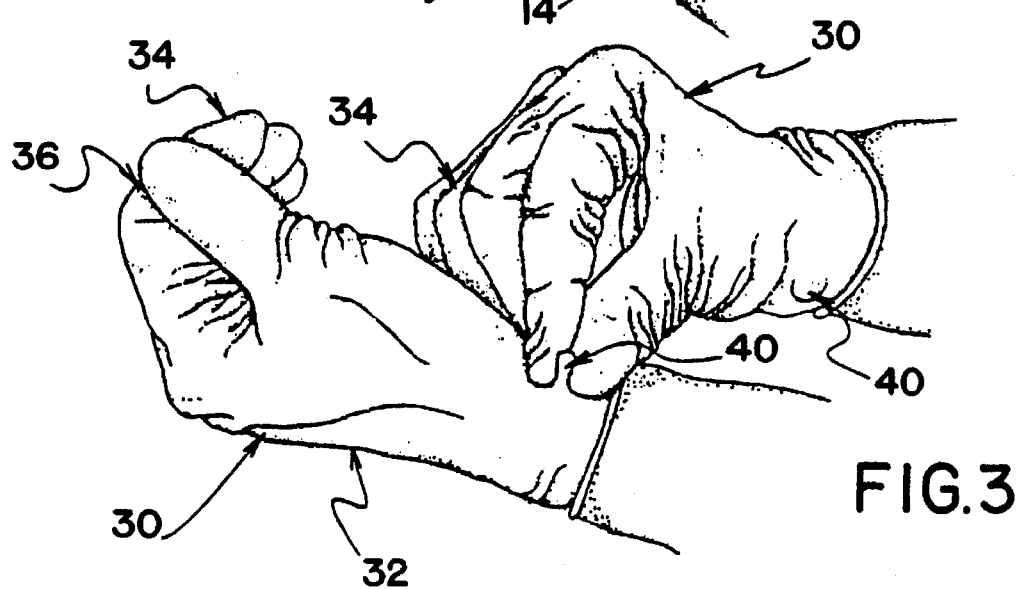
FIG. 3 is an axonometric view of a disposable, elastomeric glove in accordance with the subject invention wherein a wearer is beginning the removal process by grasping a protrusion or tab between the cuff and base of the thumb with a thumb and index finger of an opposing hand.

A pair of disposable elastomeric gloves in accordance with the subject invention is disclosed in connection with FIG. 3. In this regard, each elastomeric glove 30 includes a body portion 32, finger portions 34 and a thumb portion 36 within a unitary envelope in a conventional manner. Each glove is composed of a relatively thin film of elastomeric material such as latex or natural rubber or a plastic composition having a property of elasticity and is designed to snugly fit over the hand of a wearer to facilitate tactile sense while isolating the hand of a wearer from contamination. When it is desired to remove the disposable, elastomeric glove the subject invention includes a protrusion 40 which is integrally joined with the glove in a location between a proximal edge of a cuff region of the glove and a wrist region of the glove in a manner which will be discussed in detail below.

Turning now to FIGS. 4 and 5, there will be seen one preferred embodiment of the subject invention. In this regard, an elastomeric glove 30 is fashioned in a conventional manner as discussed above and includes a body portion having a generally flat surface 42 covering a wearer's palm and an opposing surface 44 covering the back of a wearer's hand. The glove includes conventional finger elements 34 and an enclosure 36 for a thumb. A cuff 46 is integrally fashioned with the body portion of the glove and is operable to extend along a wearer's wrist. The cuff segment 46 typically terminates with a beaded ring 48 defining the proximal end of the elastomeric glove. The bead 48 snugly surrounds a wearer's wrist and is designed to prevent contaminants from entering an interior portion of the glove around the region of the wrist.

The subject inventive glove includes means for facilely removing or doffing or adjusting the glove as discussed in connection with FIG. 3. In this regard, a protrusion 50 is depicted in FIG. 4 having the general shape of a cone with a rounded apex. The protrusion 50 includes a generally elliptical shaped base 52 and side segments 54, note FIG. 5. The protrusion 50 terminates at a rounded apex 56 and, as depicted in cross section in FIG. 5, the protrusion is a generally hollow thin film extension of the cuff region of the glove. The protrusion 50 is mounted in a location between the proximal edge or lip 48 of the cuff 46 and a base 58 of a wearer's thumb. This location enables a wearer to peel the glove cuff and glove over a wearer's abductor pollicis longus muscle without binding of the edge 48 of the cuff upon a wearer's wrist.

Although an elliptical base is preferred, a circular base can be utilized to advantage. In addition, the protrusion 50 is reversible and may be extended in an opposite direction such that the glove may be turned inside out and utilized on an opposite hand. The foregoing discussion in connection with FIGS. 4–5 depicts one embodiment of the subject invention. Alternative configurations of the protrusion are fully disclosed in my parent U.S. application Ser. No. 07/916,437, entitled "Disposable, Elastomeric Glove."

Turning to FIG. 6, there is depicted a plan view of a hand wearing a disposable, elastomeric glove in accordance with yet another embodiment of the invention. In this, an elastomeric glove 30 is composed of a conventional body portion 60, fingers 62 and thumb portion 64. The body 60 includes a palm segment 66 and a corresponding back of the hand segment (not shown). In addition, a cuff region 68 extends from the proximal location of the body portion and terminates in an annular rib or bead 70 operable to snugly engage a wearer's wrist. In this embodiment, a protrusion 72 is positioned between a bead portion 70 and a base of the thumb segment 64 of the glove cuff. This protrusion 72 may be fashioned in the configuration of embodiments depicted in FIGS. 4–5 or equivalent. The location of this protrusion 72 is at the edge of the glove as it lays flat in the manner shown in FIG. 6. Thus this particular arrangement may be advantageously utilized as an ambidextrous glove such that it may be fitted onto a wearer's left hand or right hand with equal facility. In either instance, however, the protrusion 72 is positioned inside the cuff bead 70 and will operably permit a wearer to grasp the protrusion 72 in a manner illustrated particularly in FIG. 3 and pull the cuff over the abductor pollicis longus muscle to facilely removing a contaminated glove.

In describing the illustrative embodiment of the subject invention, with respect to FIGS. 3–5, it has been found that it is advantageous to locate a protrusion in a generally rectangular area of the glove which occupies the same side of the glove as the thumb segment of the glove. Referring specifically again to FIG. 6, a first imaginary line 74 has been drawn as a general extension of the middle finger of the wearer which tends to bisect the wearer's wrist and the palm of the wearer's hand. This first imaginary line 74 has a companion parallel line 76 which extends along an outer edge of the wearer's wrist in the direction of the wearer's thumb. A further imaginary line 78 may be extended transversely across a wearer's wrist at the base of the thumb 64 and a parallel line 80 extends inside the annular bead at the proximal cuff region of the glove. The imaginary lines 74, 76, 78, and 80 operably define a generally rectangular region 82 which advantageously is a preferred location for locating the protrusion of any of the embodiments depicted in FIGS. 4–18, and equivalent embodiments thereof. In this it will be appreciated that a portion of the tab may extend outside the region 82, however, at least a central portion of the tab will be within the region 82 or on its boundary. With this positioning a wearer may advantageously grasp the protrusion and pull it over the abductor pollicis longus muscle to rapidly remove or doff the glove following use.

Figure 7:
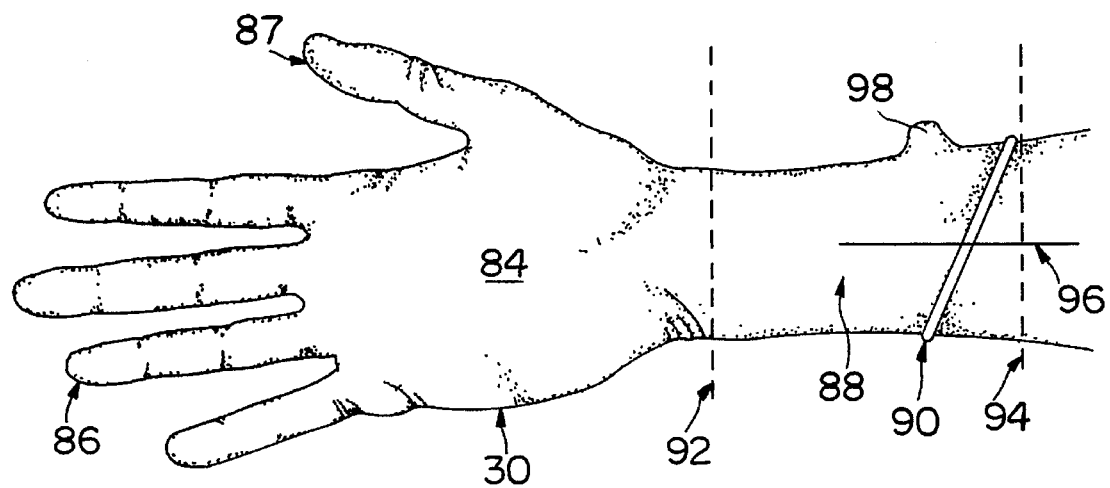
FIG. 7 is an axonometric view of a disposable, elastomeric glove in accordance with the subject invention having a protrusion and an angled cuff portion for facilitating glove removal.

Referring now to FIG. 7, there is shown a plan view of a disposable, elastomeric glove 30 which provides for an alternative cuff design. In this embodiment of the invention, elastomeric glove 30 is composed of a conventional body portion 84, fingers 86 and thumb portion 87. In addition, a cuff region 88 extends from the proximal location of the body portion and terminates in an annular rib or bead 90 operable to snugly engage a wearer's arm. In some disposable, elastomeric gloves—for example, surgical gloves-the cuff region 88 is extended an elongated distance A two to three times that of a conventional elastomeric glove in order to provide maximize protection and coverage over the sleeve of a surgical gown. The distance A is defined by a first imaginary line 92 drawn to extend transversely across a wearer's wrist at the base of the thumb 87 and a parallel imaginary line 94 extending tangentially from the most distal portion of the annular bead 90 at the proximal cuff region of the glove. In order to provide for an extended cuff portion 88 for enhanced glove coverage and easy removal, an alternative cuff edge is provided. In this, the bead 90, which defines the edge of the cuff, is angled with respect to the imaginary line 94. The imaginary line 92 bisects an imaginary line 96 drawn at the midsection of the cuff region in a manner identical to line 74 of FIG. 7 described below. The angled cuff 88 allows the elastomeric material of the extended cuff to roll easily and peel off the wrist portion without bunching or binding.

A protrusion 98 allows for gripping of the cuff portion in an identical manner disclosed with respect to FIGS. 3–6. The protrusion 98 may be formed in the manner described with reference to any of the preceding embodiments or those disclosed in my parent U.S. application Ser. No. 07/916,437, entitled "Disposable, Elastomeric Glove." The zone of optimum placement for the protrusion in the extended cuff embodiment is similar to that described with reference to FIG. 6 except the protrusion is preferably located closer to imaginary line 94 than imaginary line 92 as shown, for example, in FIG. 7. Moreover, if the protrusion is located upon the inner cuff edge as shown in FIG. 7, the glove will function as an ambidextrous glove capable of being worn on both the right and left hand of a user.

Figure 8:
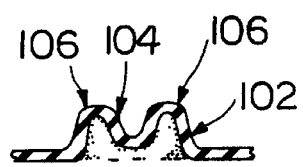
FIG. 8 is an axonometric view disclosing still another embodiment of the invention wherein a glove removal protrusion is fabricated as a ridge and valley configuration.
Figure 9:
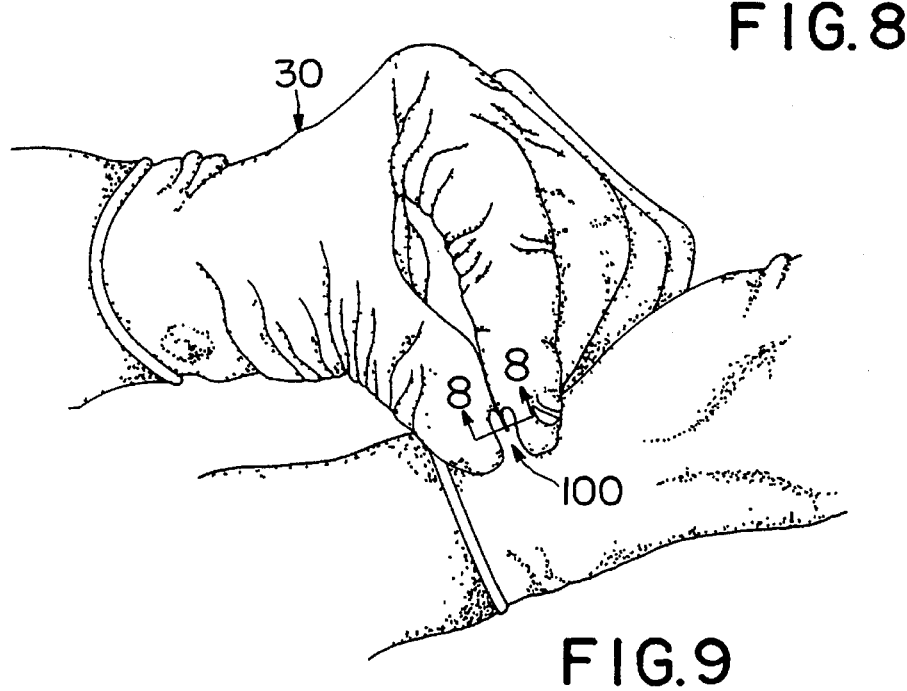
FIG. 9 is an enlarged, partial cross-sectional view, taken along section line 9—9 in FIG. 8, and discloses a ridge and valley configuration for the removal protrusion.
Figure 10:
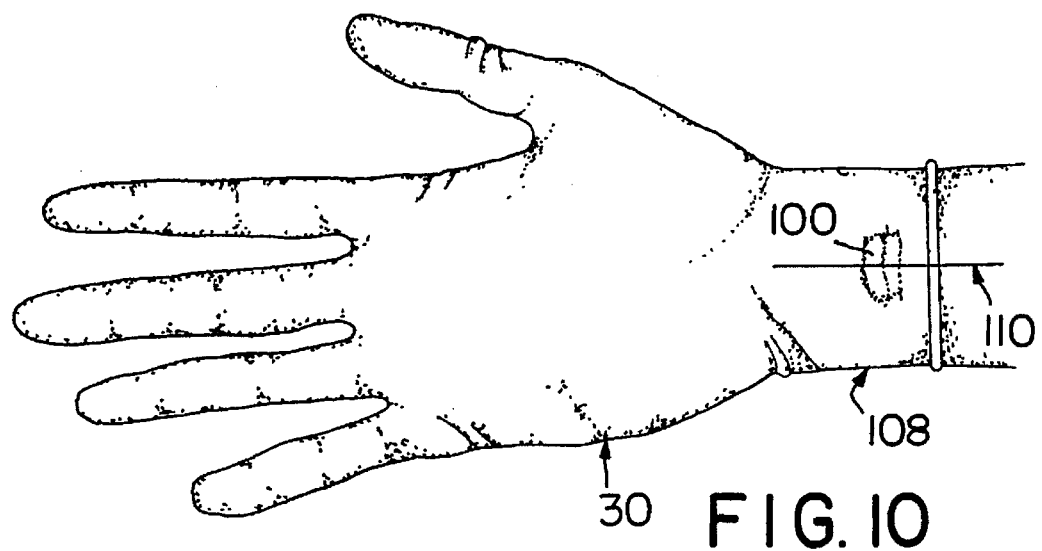
FIG. 10 is a plan view of a disposable, elastomeric glove showing the optimal placement of a protrusion for enhancing removal in accordance with an alternative glove design.

FIGS. 8, 9, and 10 disclose yet another embodiment of the invention wherein a disposable elastomeric glove 30 is fashioned with a protrusion 100 operable to facilitate removal or adjustment of the glove with respect to a wearer's hand. In this specific embodiment, as particularly shown in FIG. 9, an elongate protrusion includes a base portion 102 and a valley portion 104 defined by a pair of ridges 106. The base portion 102 of the protrusion 100 extends a sufficient distance above the surface of the cuff to allow for the creation of a gripping bead when a wearer grasps the protrusion. When it is desired to remove the elastomeric glove 30, the wearer grasps the protrusion 100 in a similar manner described with reference to FIG. 3 and peels the glove cuff and glove over the abductor pollicis longus muscle. Again, the protrusion is reversible and may extend in an opposite direction.

As shown in FIG. 10, the protrusion 100 is located in a mid-portion of the cuff 108. This design allows for a removal technique which optimizes safety and wearer protection. As shown in FIG. 11, the wearer of the gloves 30 places the palms of his/her hands adjacent one another such that the thumb and index fingers of the opposing hands grasp the protrusion 100 of the glove 30 worn on the opposite hand. The wearer next pulls the protrusions 100 on opposite gloves 30 towards one another as indicated by arrows B. While pulling outwardly with each arm, the wearer peels each glove 30 using the protrusion 100 so as to maneuver the glove over the abductor pollicis longus muscle and hand in order to complete simultaneous glove removal. Significantly, in pulling the protrusions 100, the wearer turns the gloves inside out as he/she peels the gloves 30 off both hands. This procedure allows glove removal without the need for touching exposed surfaces of one hand to contaminated portions of a glove worn on the other hand.

The protrusion 100 may be of any of the forms disclosed above or those disclosed in my parent U.S. application Ser. No. 07/916,437, entitled "Disposable, Elastomeric Glove." As shown in FIG. 11, however, the glove utilizes the protrusion disclosed with reference to FIGS. 8 & 9. The protrusion 100 is located in a mid-section of the cuff portion 108 of the glove 30. The placement of the protrusion 108 in this embodiment is described with reference to the imaginary line 100 drawn at the mid-section of the cuff region. At least a portion of the protrusion 100 is contained within the optimal zone 82, described with reference to FIG. 6, defined in part by imaginary line 110. The protrusion may be located entirely within the optimal zone 82 just adjacent the imaginary line 110. Preferably, the protrusion is bisected by the imaginary line 110 as shown in FIG. 10. This assures quick and easy grasping by the wearer's thumb and index finger. When using the ridge and valley protrusion described with reference to FIGS. 8–9, a longitudinal axis of the ridge and valley is substantially perpendicular to the imaginary line 110 as shown in FIG. 10. In order to provide for a disposable, elastomeric glove 30 that is ambidextrous, the glove 30 may be provided with two protrusions 100 located on opposing sides of the cuff 112 as shown in FIG. 12. This is an ambidextrous design in that one glove design may be worn on either the left or right hand while enabling a double or simultaneous removal procedure from the inside cuff region as depicted in FIG. 11. This design allows the wearer to place the gloves on their hands with out regard to whether the protrusion is properly positioned on the inner cuff.

SUMMARY OF MAJOR ADVANTAGES OF THE INVENTION

In describing a disposable, elastomeric glove in accordance with preferred embodiments of the invention, those skilled in the art will recognize several advantages which singularly distinguish the invention from the heretofore known prior art. A particular advantage is the provision of a protrusion located between the proximal cuff rim or bead of a glove and the base of the wearer's thumb such that the cuff may be facilely pulled over the abductor pollicis longus muscle to rapidly remove the glove without binding.

The region 82 of the glove may be advantageously used to mount the protrusion to optimally pull the cuff of the glove over the abductor pollicis longus muscle. In addition, the subject protrusion may be readily manufactured by conventional elastomeric glove dipping techniques and is positioned away from interfering conflict with procedures normally attendant with those who need to wear protective elastomeric gloves.

The protrusion may be advantageously located so as to enable removal of the gloves worn on both hands simultaneously. In this, the gloves may be removed from the wearer's hands without contacting exposed portions of one hand with a contaminated glove worn on the other hand. Disposable, elastomeric gloves having an extended cuff portion are further provided with an angled distal end portion which enhances the peel affect of the glove on removal.

The subject protrusion feature while serving a primary function of enhancing a removal procedure may be synergistically utilized as a glove an adjustment tool during a normal procedure.

The specific embodiments of the subject invention as depicted in the drawings are illustrative and are not intended to be exhaustive of all equivalence thereof. In these embodiments a protrusion is provided to enable a wearer to remove a snug fitting glove in a smooth removal stroke without binding or undue force.

In describing the invention, reference has been made to preferred embodiments. Those skilled in the art, however, and familiar with the disclosure of the subject invention may recognize additions, deletions, substitution modifications and/or other changes which will fall within the purview of the invention as defined in the following claims.

What is claimed is:

1. A disposable elastomeric hand enclosure worn to prevent the transmission of chemical or biological contamination with a safe doffing provision, the hand enclosure comprising:

a hollow, seamless, hand enclosure;

an open proximal end, and a smooth, peripheral cuff portion at said proximal end, said peripheral cuff portion having a peripheral proximal edge; and means for removing said hand enclosure from a wearer's hand comprising a protuberance positioned upon said cuff of the hand enclosure and located substantially upon a zone of an inner wrist portion of said cuff between a proximal edge of the cuff and a first imaginary line extending transversely across the cuff of the hand enclosure at the base of the wearer's thumb, and between a second imaginary line longitudinally bisecting a palm surface of a body portion of the hand enclosure and a longitudinal edge of the hand enclosure cuff extending generally parallel with the second imaginary line; and said peripheral proximal edge of said cuff being slanted from said longitudinal edge of the hand enclosure cuff that defines said zone in a direction toward said body portion of the hand enclosure;

wherein a wearer of said hand enclosure may operably grasp said means for removing between a thumb and index finger of an opposing hand and peel the hand enclosure over the base of a thumb of the hand enclosure and invert the hand enclosure with a facile removal process.

2. A disposable, elastomeric hand enclosure as defined in claim 1 wherein the protuberance is located upon said longitudinal edge in order to provide for an ambidextrous hand enclosure.

3. A disposable elastomeric hand enclosure as defined in claim 1 wherein said protuberance comprises:

an elongated protrusion having a generally rectangular base portion as viewed in plan and a valley portion defined by a pair of ridges.

4. A disposable elastomeric hand enclosure worn to prevent the transmission of chemical or biological contamination with a safe doffing provision, said hand enclosure comprising:

a hollow, seamless, hand enclosure;

an open proximal end, and a smooth, peripheral cuff portion at said proximal end;

means for removing said hand enclosure from a wearer's hand comprising a distinct protuberance positioned upon said cuff of the hand enclosure and located substantially upon an inner wrist portion of said cuff between a proximal edge of the cuff and a first imaginary line extending transversely across the cuff of the hand enclosure at the base of the wearer's thumb, wherein the location of said protuberance is further defined by a second imaginary line longitudinally bisecting a palm surface of a body portion of the hand enclosure and wherein at least a portion of said protuberance is located on the secondary imaginary line; and wherein a wearer of said hand enclosure may simultaneously remove a worn pair of said hand enclosure by positioning the palms of the wearer's hands adjacent one another and simultaneously grasping said means for removing of said pair of hand enclosures between a thumb and index finger of opposing hands and peeling the hand enclosures over the base of thumbs of the hand enclosures and invert the hand enclosures with a facile removal process.

5. A disposable, elastomeric hand enclosure as defined in claim 4 wherein:

a second protuberance is located on an opposing cuff portion opposite the first protuberance so as to appear as a mirror image whereby the disposable, elastomeric hand enclosure functions as an ambidextrous hand enclosure.

6. A disposable, elastomeric hand enclosure as defined in claim 4 wherein:

said protuberance is located on the secondary imaginary line such that the protuberance is bi-sected by said second imaginary line.

7. A method of removing a pair of disposable elastomeric gloves worn to prevent the transmission of chemical or biological contamination to the hands of a wearer, said gloves having identical configurations comprising a hollow, seamless, hand enclosure, an open proximal end, and a smooth, peripheral cuff portion at said proximal end, said gloves further comprising a distinct protuberance positioned upon said cuff of the hand enclosure and located substantially upon an inner wrist portion of said cuff between a proximal edge of the cuff and a first imaginary line extending transversely across the cuff of the hand enclosure at the base of the wearer's thumb, said method of glove removal comprising the steps of:

positioning the hand enclosures of the gloves adjacent one another such that the palms of the wearer's hands face each other:

grasping between the thumb and index fingers of one hand the distinct protrusion located on the glove cuff worn on the other hand and grasping between the thumb and index fingers of the other hand the distinct protrusion located on the glove cuff worn on the one hand;

moving the wearer's hands away from each other while maintaining grasp of the protrusions; and simultaneously peeling each glove over the abductor pollicis longus muscle and hand while pulling the protrusion in order to complete simultaneous removal of the gloves, wherein simultaneous glove removal may be achieved without the need for touching exposed surfaces of one hand with contaminated portions of the glove worn on the other hand.

* * * * *